(12) United States Patent
Ayame et al.

(10) Patent No.: US 8,040,373 B2
(45) Date of Patent: Oct. 18, 2011

(54) ENDOSCOPE SPECTRAL IMAGE SYSTEM APPARATUS

(75) Inventors: Daisuke Ayame, Saitama (JP); Kazunori Abe, Saitama (JP); Shinji Takeuchi, Saitama (JP)

(73) Assignee: Fujinon Corporation, Saitama (JP)

( * ) Notice: Subject to any disclaimer, the term of this patent is extended or adjusted under 35 U.S.C. 154(b) by 1420 days.

(21) Appl. No.: 11/377,272

(22) Filed: Mar. 17, 2006

(65) Prior Publication Data

US 2006/0252988 A1 Nov. 9, 2006

(30) Foreign Application Priority Data

Mar. 18, 2005 (JP) ................ P.2005-080426

(51) Int. Cl.
*A61B 1/04* (2006.01)
*A61B 6/00* (2006.01)
*A61B 1/06* (2006.01)
(52) U.S. Cl. ........... 348/71; 600/181; 600/160; 600/476
(58) Field of Classification Search .............. 348/65, 348/70, 71; 600/160, 178, 181, 476
See application file for complete search history.

(56) References Cited

U.S. PATENT DOCUMENTS

| | | | |
|---|---|---|---|
| 4,885,634 A | 12/1989 | Yabe | |
| 4,926,247 A | 5/1990 | Nagasaki et al. | |
| 5,331,551 A | 7/1994 | Tsuruoka et al. | |
| 5,408,263 A | 4/1995 | Kikuchi et al. | |
| 7,393,321 B2 * | 7/2008 | Doguchi et al. | 600/109 |
| 7,573,499 B2 * | 8/2009 | Doguchi et al. | 348/65 |
| 7,800,656 B2 * | 9/2010 | Takeuchi et al. | 348/222.1 |
| 7,850,599 B2 * | 12/2010 | Takeuchi et al. | 600/109 |
| 7,944,466 B2 * | 5/2011 | Abe et al. | 348/71 |
| 2003/0001952 A1 | 1/2003 | Iida et al. | |
| 2004/0141054 A1 | 7/2004 | Mochida et al. | |
| 2004/0225222 A1 * | 11/2004 | Zeng et al. | 600/476 |
| 2004/0257438 A1 * | 12/2004 | Doguchi et al. | 348/65 |
| 2005/0010081 A1 * | 1/2005 | Doguchi et al. | 600/109 |
| 2006/0197830 A1 * | 9/2006 | Takeuchi et al. | 348/65 |
| 2006/0197831 A1 * | 9/2006 | Takeuchi et al. | 348/70 |

(Continued)

FOREIGN PATENT DOCUMENTS

JP 64-17621 1/1989

(Continued)

OTHER PUBLICATIONS

Miyake, Tokyo University Printing Association Foundation, pp. 148-153.

(Continued)

*Primary Examiner* — David Ometz
*Assistant Examiner* — Dillon Durnford Geszvain
(74) *Attorney, Agent, or Firm* — Birch, Stewart, Kolasch and Birch, LLP

(57) ABSTRACT

An endoscope spectral image system is provided and includes: an image recording apparatus for recording a color image provided by using a scope; and a processor apparatus, in which spectroscopic characteristic information including a spectroscopic characteristic of CCD is output from the processor apparatus to the image recording apparatus along with color image data. At the image recording apparatus, matrix data in correspondence with the spectroscopic characteristic information is selected to be read from a plurality of matrix data stored in a memory, matrix operation by the matrix data and color image data is carried out at a spectral image-forming circuit, and a spectral image formed by signals of arbitrarily selected wavelength regions is provided.

4 Claims, 8 Drawing Sheets

U.S. PATENT DOCUMENTS

| | | | |
|---|---|---|---|
| 2006/0198551 A1* | 9/2006 | Abe et al. | 382/128 |
| 2006/0211915 A1* | 9/2006 | Takeuchi et al. | 600/109 |
| 2006/0253036 A1* | 11/2006 | Takeuchi et al. | 600/478 |

FOREIGN PATENT DOCUMENTS

| | | |
|---|---|---|
| JP | 64-43227 | 2/1989 |
| JP | 6-90900 | 4/1994 |
| JP | 6-335449 | 12/1994 |
| JP | 2000-14629 | 1/2000 |
| JP | 2000-221417 | 8/2000 |
| JP | 2000-350231 | 12/2000 |
| JP | 2001-112712 | 4/2001 |
| JP | 2003-93336 A | 4/2003 |
| JP | 2004-194993 | 7/2004 |

OTHER PUBLICATIONS

Japanese Notification of Reasons for Refusal, Jul. 1, 2010.

* cited by examiner

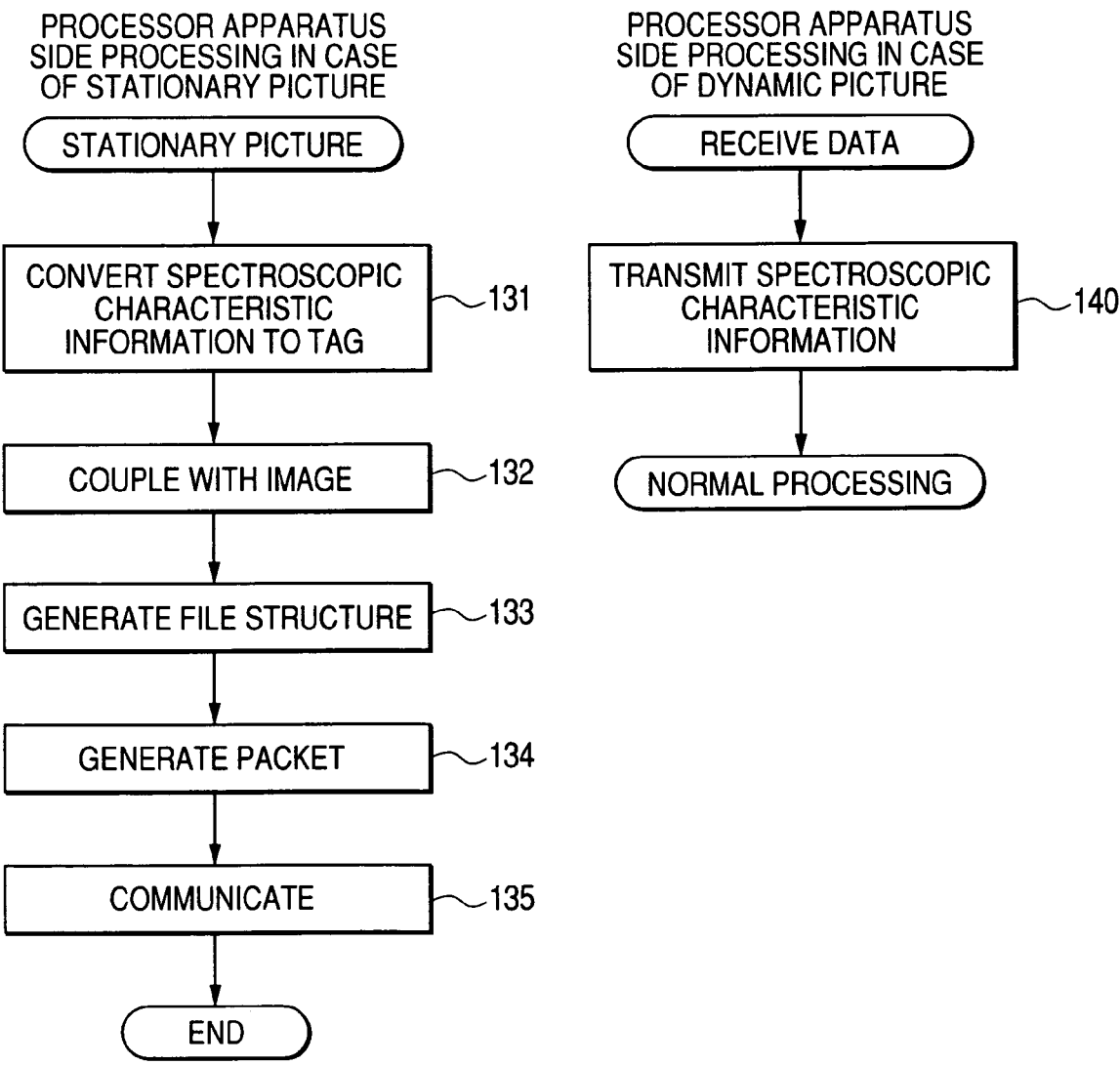

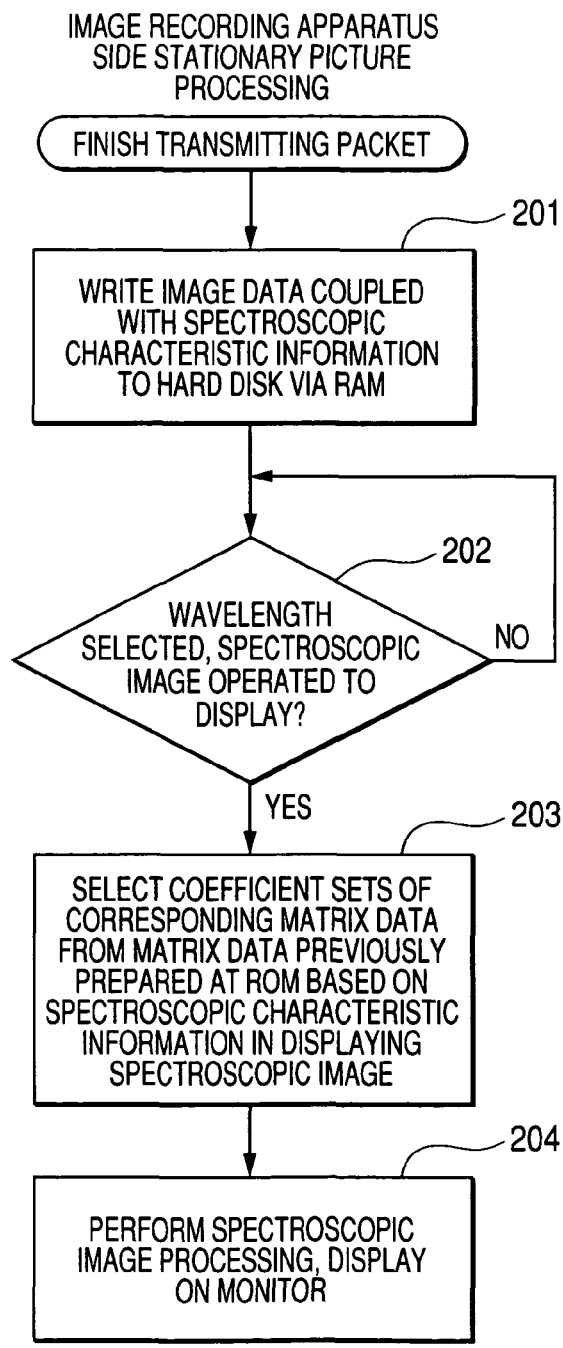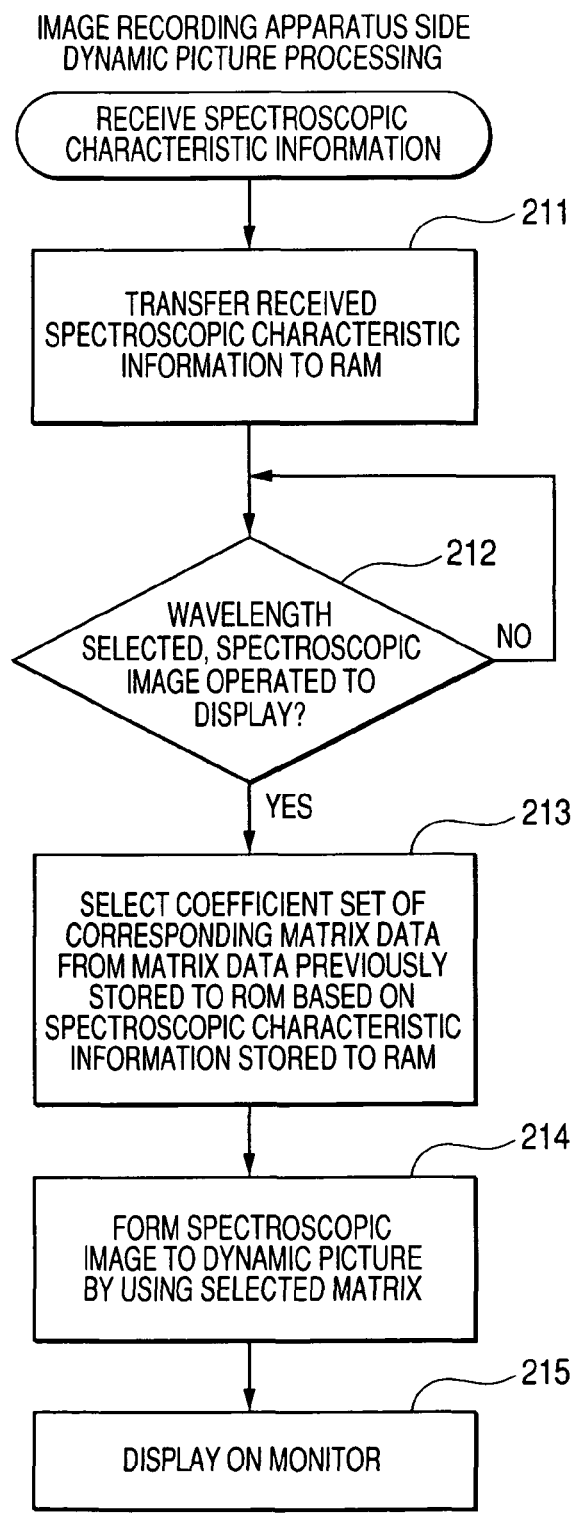

ENDOSCOPE SPECTRAL IMAGE SYSTEM APPARATUS

FIELD OF THE INVENTION

The present invention relates to an endoscope system apparatus, particularly relates to a constitution used in a medical field for forming and displaying a spectral image (image) comprising image information of an arbitrary selected wavelength region.

BACKGROUND OF THE INVENTION

In recent years, in an electronic endoscope apparatus using a solid state image sensor, attention is attracted to spectroscopic imaging combined with a narrow band pass filter, that is, a narrow band filter incorporated electronic endoscope apparatus (Narrow Band Imaging-NBI) based on a prediction of a spectroscopic reflectance in the digesting organ (stomach mucosa or the like). According to the apparatus, three band pass filters of narrow (wavelength) bands are provided in place of a rotating filter of R (red), G (green), B (blue) of a face sequential type, and a spectral image is formed by successively outputting illuminating light by way of the narrow band path filters and processing three signals provided by the illuminating light while changing respective weights thereof similar to a case of R, G, B (RGB) signals. According to the spectral image, in the digesting organ of the stomach, the large intestine or the like, a fine structure which cannot be provided in a background art is extracted.

Meanwhile, it has been proposed to form a spectral image by operation processing based on the image signal provided by white light not by the face sequential type using the narrow band pass filters but by a simultaneous type for arranging a color filter of a small mosaic to a solid state image sensor as shown by JP-A-2003-93336 and Tokyo University Printing Association Foundation 'Analysis and Evaluation of Digital Color Image' by MIYAKE, yoichi (P148 through P153). According thereto, a relationship between respective color sensitivity characteristics of RGB which are formed into numerical value data and a spectroscopic characteristic of a specific narrow band pass filter which is formed into numerical value data is calculated as matrix data (coefficient set) and by operation of the matrix data and RGB signals, a spectral image signal provided by way of the narrow band pass filter is pseudonically provided. When the spectral image is formed by such an operation, it is not necessary to prepare a plurality of filters in correspondence with a desired band pass region, an interchanging arrangement thereof is dispensed with and therefore, large-sized formation of the apparatus is avoided and low cost formation thereof can be achieved.

Meanwhile, according to a spectral image extracting a specific fine structure or the like of an object, it is necessary to select a preferable wavelength region or adjusting the selected wavelength region and there is a case in which a necessary and sufficient spectral image cannot be provided in inspection by an endoscope in a limited time period. Further, it is necessary to observe and diagnose the spectral image in details by comparing with a normal color image and when a spectral image having an arbitrary wavelength region can be formed and displayed after inspection by the endoscope, an apparatus having an excellent way of use can be provided.

Further, in the operation processing of the spectral image by the endoscope apparatus, for example, color image signals of RGB constituting a basis thereof differs by a spectroscopic sensitivity characteristic including a kind of a color filter of an imaging element (solid state image sensor or the like), a kind of a light source, a spectroscopic sensitivity characteristic of an optical system member of the endoscope of a light guide or the like to pose a problem that such differences in the spectroscopic characteristics of the endoscope of the light source effect an influence on reproducibility on the same wavelength region. That is, there are CCDs constituting solid state image sensors of a complementally color type having color filters of Mg, Ye, Cy, G and a primary color type having color filters of RGB, further, even in the CCD of the same kind, the spectroscopic sensitivity characteristic differs by an individual difference. FIG. 9 shows an example of spectroscopic sensitivity characteristics of color filters of primary color type CCD, respective spectroscopic sensitivities of the R, G, B color filters differ by an individual difference of CCD, in an operation processing using a single matrix data, the difference in the spectroscopic characteristics is reflected to an operation result and the spectral image having reproducibility cannot be provided.

Further, a spectroscopic characteristic of illuminating light differs by an aperture amount of a diaphragm blade in the light source apparatus owing to chromatic aberration of lenses, there is constituted a characteristic in which the more the light amount is reduced, the more the red color component is gradually cut from a long wavelength side to pose a problem that the reproducibility of the spectral image is deteriorated even by the spectroscopic characteristic of the illuminating light.

SUMMARY OF THE INVENTION

An object of an illustrative, non-limiting embodiment of the present invention is to provide an endoscope spectral image system apparatus capable of forming and displaying a spectral image of an arbitrary wavelength region after inspection by an endoscope, capable of forming a spectral image having excellent reproducibility in the same wavelength region even when a spectroscopic characteristic of an imaging element or an endoscope or a spectroscopic characteristic of a light source or illuminating light differs and having an excellent way of use.

The above object are accomplished with the following constitutions:

(1) An exemplary embodiment of an endoscope system apparatus (an endoscope spectral image system apparatus) of the invention includes: a signal processor for forming a color image of an object based on an output from an imaging element mounted to an endoscope (the signal processor is arranged at the endoscope or a processor apparatus); and an image recording apparatus (filing apparatus or the like), which is constituted separately from the signal processor, for recording the color image output from the signal processor, wherein the signal processor includes an information-outputting circuit for outputting spectroscopic characteristic information for forming a spectral image, the spectroscopic characteristic information including at least spectroscopic characteristic (sensitivity) of the imaging element, and the image recording apparatus includes: a storing portion for storing a plurality of matrix data (coefficient data) for forming the spectral image based on the color image data, the matrix data corresponding to the spectroscopic characteristic information output from the information-outputting circuit; and a spectral image-forming (generating) circuit for performing a matrix operation based on the color image data and the matrix data stored in the storing portion so as to form the spectral image with respect to an arbitrarily selected wavelength region.

(2) The endoscope system apparatus of the above (1) further includes a light source apparatus for irradiating the object with illuminating light through the endoscope, wherein the spectroscopic characteristic in accordance with a kind of a light source (Xenon lamp, halogen lamp) of the light source apparatus is supplied to the image recording apparatus as the spectroscopic characteristic information, and the spectral image is formed by selecting a matrix data in accordance with the kind of the light source.

(3) The endoscope system apparatus of the above (2), wherein the light source apparatus including a diaphragm position-detecting sensor for detecting a diaphragm position of an illuminating light when the color image is formed, the diaphragm position output from the diaphragm position-detecting sensor is supplied to the image recording apparatus as the spectroscopic characteristic information, and the spectral image is formed by selecting a matrix data in accordance with the diaphragm position.

(4) The endoscope system apparatus of any one of the above (1) to (3), wherein the image recording apparatus is detachably connected with a display, and the color image and the spectral image are made to be able to be displayed on the display.

According to the above-described constitution, the spectroscopic characteristic information is supplied from the signal processor to the image recording apparatus along with the normal color image data, at the image recording apparatus, the matrix data (coefficient set) in correspondence with the spectroscopic characteristic information is read from the plurality of matrix data stored to the storing portion, and the spectral image is formed by the matrix operation based on the data. That is, the matrix data includes coefficients for calculating $\lambda 1$, $\lambda 2$, $\lambda 3$ signals of wavelength narrow bands (components) by the matrix operation from, for example, RGB signals (may be other signals), or 61 of wavelength region parameters (coefficient sets p1 through p61) constituted by dividing a wavelength region from 400 nm to 700 nm by an interval of 5 nm, and a plurality of table data comprising 61 of the coefficient sets are prepared in accordance with the spectroscopic characteristic. Further, when the operator selects three wavelength regions $\lambda 1$, $\lambda 2$, $\lambda 3$ (may be one wavelength region), $\lambda 1$, $\lambda 2$, $\lambda 3$ signals are formed from matrix data (coefficient set) in correspondence with the three wavelength regions and the RGB signals output from DVP, DSP ort the like, the spectral image having excellent reproducibility is formed by the $\lambda 1$, $\lambda 2$, $\lambda 3$ signals and displayed on a monitor or the like. That is, according to the image recording apparatus, not only the recorded normal image (stationary picture and dynamic picture) is reproduced and displayed, but also, based on the normal image, the spectral image (stationary picture and dynamic picture) in consideration of the spectroscopic characteristic of the endoscope (CCD) can be generated and displayed.

According to the constitution of the above (2), the matrix data in accordance with a difference of the spectroscopic characteristic of a Xenon lamp or a halogen lamp is read, according to the constitution of claim 3, the matrix data divided by, for example, 6 stages, in accordance with the diaphragm position (state) and in accordance with the spectroscopic characteristics of the 6 stages is read, the spectral image in accordance with the spectroscopic characteristics is formed and therefore, the reproducibility is further improved.

According to an exemplary embodiment of the endoscope apparatus of the invention, by holding the spectroscopic characteristic information along with the normal color image, after inspection by the endoscope, the spectral image of the arbitrary wavelength region can be formed and displayed and object image information useful for diagnosis or the like can be provided. Further, even when the spectroscopic characteristic of the imaging element or the endoscope taking the image of the normal color image, or the spectroscopic characteristic of the light source or the illuminating light differs, the spectral image having the excellent reproducibility which is not influenced by the differences of the spectroscopic characteristics can be formed and the apparatus having an excellent way of use can be provided.

BRIEF DESCRIPTION OF THE DRAWINGS

FIGS. 6A and 6B illustrate flowcharts showing detailed contents a stationary picture transmitting processing (FIG. 6A) and a processing in case of a dynamic picture (FIG. 6B) in FIG. 5 in the processing of the spectroscopic characteristic information on the side of the processor apparatus of an exemplary embodiment of the invention.

FIGS. 7A and 7B illustrate flowcharts showing a stationary picture processing (FIG. 7A) and a dynamic picture processing (FIG. 7B) on a side of the image recording apparatus of an exemplary embodiment of the invention.

DETAILED DESCRIPTION OF THE INVENTION

Figure 1:
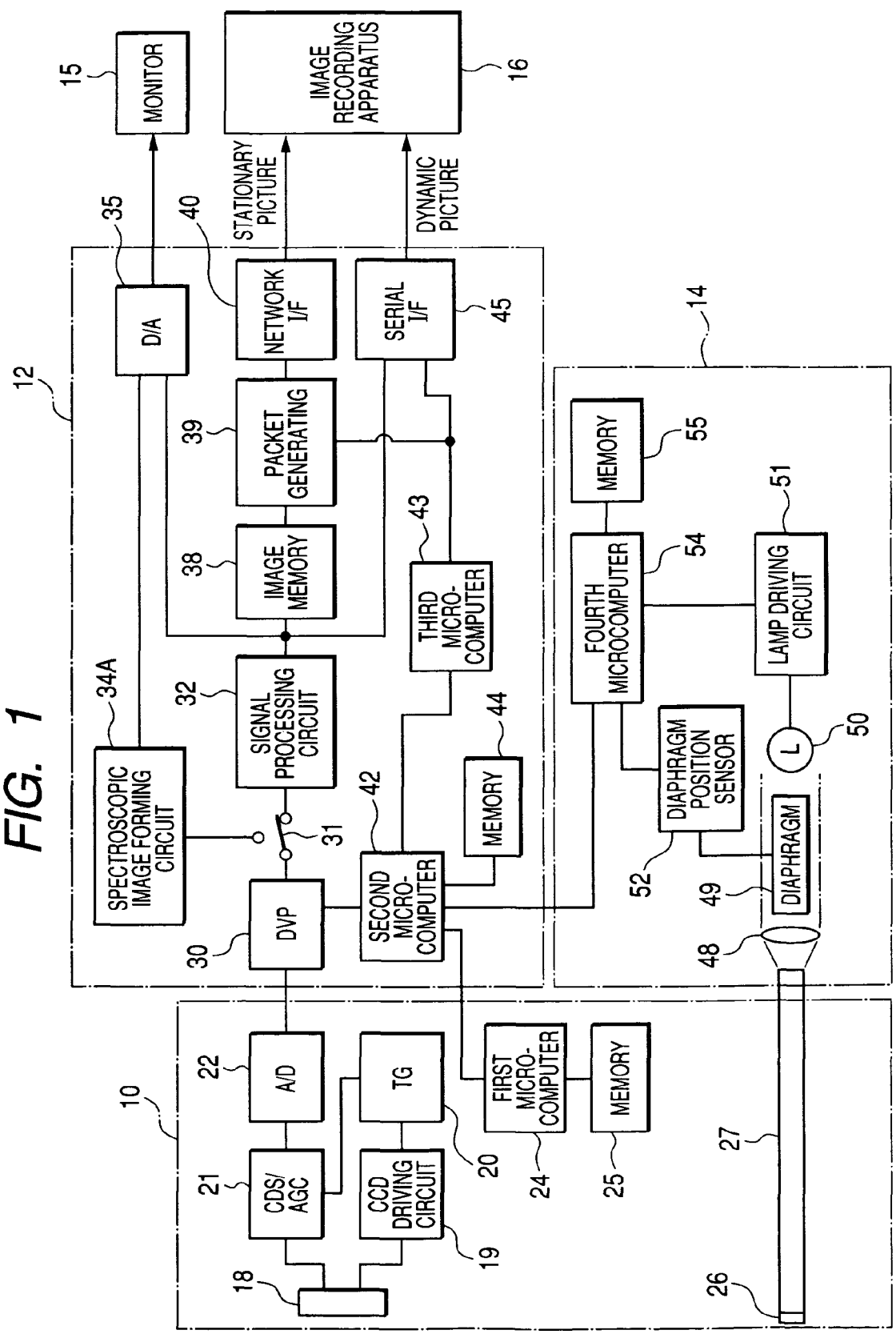
FIG. 1 is a block diagram showing a total constitution of an endoscope spectral image system apparatus according to an exemplary embodiment of the invention.

FIG. 1 through FIGS. 4A and 4B show a constitution of an endoscope (electronic endoscope) spectral image system apparatus according to an exemplary embodiment, as shown by FIG. 1, the apparatus is constituted to connect a scope (electronic endoscope) 10 detachably from a processor apparatus 12 and a light source apparatus 14, the processor apparatus 12 is connected with a monitor 15 and an image recording apparatus (or filing apparatus) 16, and the monitor 15 is connected also to the image recording and displaying (recording and reproducing) apparatus 16. The image recording apparatus 16 can be constituted by a personal computer or the like having a keyboard, a mouse. Further, there is also a case in which the light source apparatus 14 is integrally constituted with the processor apparatus 12, further, there is also a case in which a main signal processing circuit at inside of the processing apparatus 12 is arranged at the scope 10.

The scope 10 is provided with CCD 18 constituting a solid state image sensor at a front end portion thereof, as the CCD 18, for example, a complementally color type having color filters of Mg (magenta), Ye (yellow), Cy (cyan), G (green) or a primary color type having color filters of RGB is used at an image taking face thereof. The CCD 18 is provided with a CCD driving circuit 19 for forming a drive pulse based on a synchronizing signal output from a timing generator (TG) 20 and is provided with a CDS/AGC (correlated double sampling/automatic gain control) circuit 21 for sampling and amplifying a picture image (image) signal input from the CCD 18, an A/D converter 22. Further, a microcomputer 24 for controlling various circuits in the scope 10 and communicating with a second microcomputer (42) at inside of the processor apparatus 12, and a memory (ROM or the like) 25 for storing a spectroscopic characteristic (spectroscopic characteristic in primary color type, complementary color type) of CCD 18, spectroscopic characteristic information of the scope 10 including spectroscopic characteristics or the like of an abject optical system, optical system members including a light guide and other identifying information are arranged. Further, the scope 10 is provided with an illuminating window 26 at a front end thereof, and the illuminating window 26 is connected to the light source apparatus 14 by a light guide 27.

On the other hand, the processor apparatus 12 is provided with a DVP (digital video processor) 30 for subjecting an image signal converted into digital to various image processing, and at the DVP 30, a Y/C signal constituted by a brightness (Y) signal and a chrominance [C (R-Y, B-Y)] signal is formed from an output signal of the CCD 18 and output. According to the embodiment, a normal image (dynamic picture and stationary picture) and a spectral image (dynamic picture and stationary picture) can selectively be formed and displayed, the DVP 30 is connected with a signal processing circuit 32 for forming a normal image by way of a switch 31 (at one terminal) for switching whether the normal image is formed or the spectral image is formed, the signal processing circuit 32 carries out a signal processing of character mix or the like for adding an image taking condition, patient information or the like to the image signal data. Other terminal of the switch 31 is arranged with a spectral image-forming circuit 34A for forming the spectral image at inside of the processor apparatus 12, a D/A converter 35 for inputting both outputs of the circuit 34A and the signal processing circuit 32, and an output of the D/A converter 35 is supplied to the monitor 15.

Further, the signal processing circuit 32 is arranged with an image memory 38 for temporarily holding a stationary picture, a packet generating circuit 39 for correlating the stationary picture and the spectroscopic characteristic information, and a network I/F (interface) 40 as a constitution for outputting the stationary picture to the image recording apparatus 16. Further, the processor apparatus 12 is provided with the second microcomputer 42 for controlling an inner circuit thereof and communicating with the first microcomputer 24, a third microcomputer 43 for carrying out similar processing, a memory 44 (ROM or the like) for storing operation information at inside of the processor apparatus 12, matrix data (Table) for forming the spectral image based on RGB signals, a serial I/F (interface) 45 for outputting a dynamic picture, the dynamic picture and the spectroscopic characteristic information are output from the serial I/F 45 and a packet for the stationary picture is output from network I/F 40. That is, scope side spectroscopic characteristic information (data) stored to the memory 25 of the scope 10 is transmitted from the first microcomputer 24 to the third microcomputer 43 by way of the second microcomputer 42, the stationary picture is added to image data at the packet generating circuit 39 and the dynamic picture is transmitted by the serial I/F 45. Therefore, the first microcomputer 24 through the third microcomputer 43 (and fourth microcomputer 50), the packet generating circuit 39 and the interfaces 40, 45 constitute information-outputting circuits. Further, the matrix data stored to the memory 44 is read by the second microcomputer 42 and is provided to the spectral image-forming circuit 34A.

Further, the light source apparatus 14 is provided with a light converging lens 48 for outputting illuminating light to the light guide 27, a diaphragm (blade) 49, a light source lamp (Xenon lamp or halogen lamp) 50, a lamp driving circuit 51 and a diaphragm position sensor 52 for detecting a drive diaphragm position of the diaphragm 49, and arranged with a memory (ROM or the like) 55 for storing information with regard to the fourth microcomputer 54, a kind of the light source lamp 50 or the like. Further, the fourth microcomputer 54 supplies the diaphragm position information (or spectroscopic characteristic information in correspondence with the diaphragm position), information of whether the light source lamp 50 is a Xenon lamp or a halogen lamp (or spectroscopic characteristic information in correspondence with the kind of lamp) to the second microcomputer 42, and the information is transmitted to the image recording apparatus 16 along with other spectroscopic characteristic information by being supplied to the third microcomputer 43.

Figure 2:
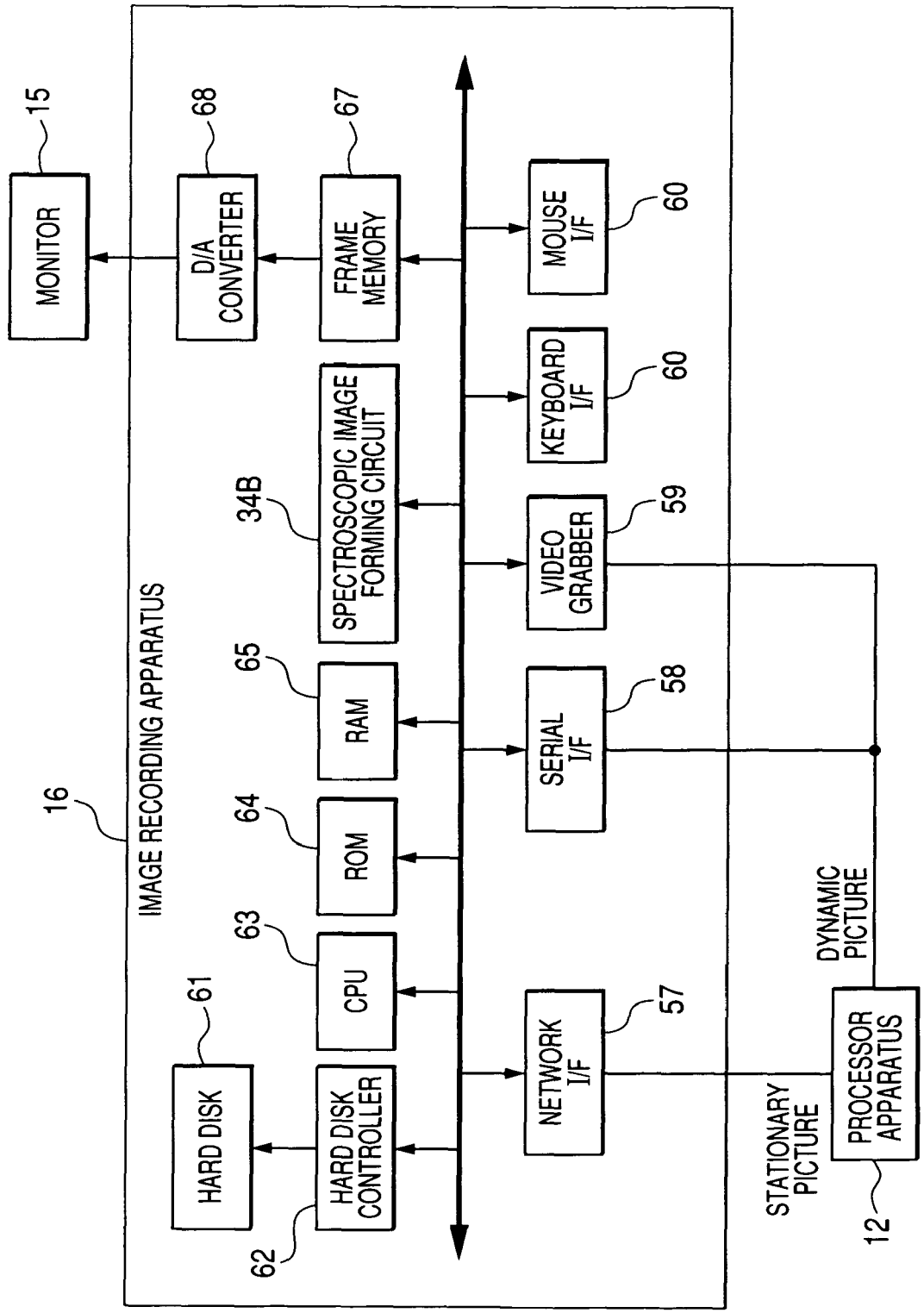
FIG. 2 is a block diagram showing a constitution of an image recording apparatus of an exemplary embodiment of the invention.

FIG. 2 shows an inner constitution of the image recording and displaying (reproducing) apparatus 16, inside of the apparatus 16 is provided with interfaces of a network I/F 57 for inputting a packet for the stationary picture, a serial I/F 58 for inputting spectroscopic characteristic information in recording the dynamic picture, a video grabber 59 for capturing the normal color image data of the dynamic picture, a keyboard I/F (interface) 60a, a mouse I/F 60b, which are connected to the processor apparatus 12, and the interfaces are connected to respective circuits, mentioned later, by way of a data path. That is, according to the image recording apparatus 16, not only the recorded normal image (both of the stationary picture and the dynamic picture) is reproduced and displayed but also the spectral image (both of the stationary picture and the dynamic picture) is formed based on the normal image to display and operation therefor is carried out by a keyboard or a mouse.

Further, the image recording apparatus 16 is provided with a hard disk 61 for storing the image, a hard disk controller 62, CPU (or microcomputer) 63 for governing to control respective circuits, ROM (Read Only Memory) 64 for storing the matrix data for forming the spectral image from the RGB signals and a plurality of matrix data (table data) in correspondence with the spectroscopic characteristic information output from the processor apparatus 12, RAM (Readable Writable Memory) 65 for inputting to process data or the like, a spectral image-forming circuit 34B for forming the spectral image by using the read matrix data, a frame memory 67 for a monitor display processing and a D/A converter 68, and an output to the D/A converter 68 is supplied to the monitor 15.

Figure 3:
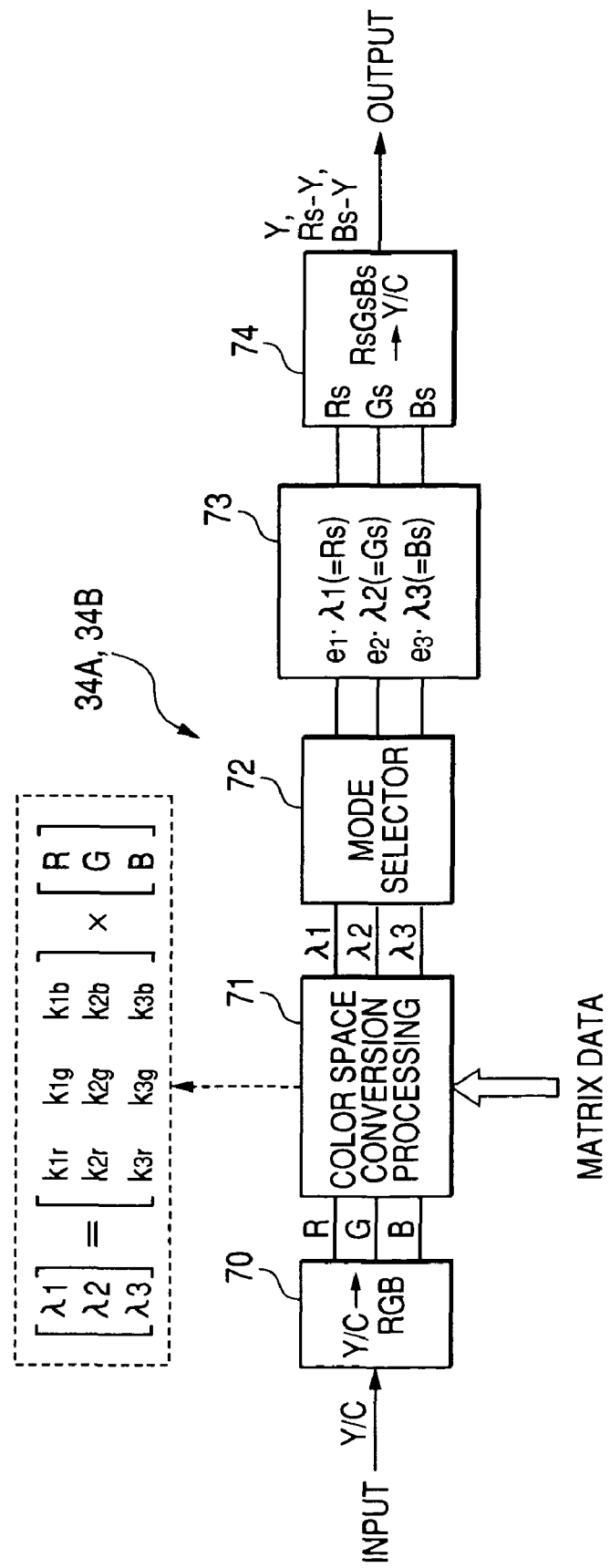
FIG. 3 is a block diagram showing a constitution of a spectral image-forming circuit of an exemplary embodiment of the invention.

FIG. 3 shows an inner constitution of the spectral image-forming circuit 34A, 34B arranged at the processor 12 and the image recording apparatus 16, the spectral image-forming circuit 34A, 34B is provided with a first color converting circuit 70 for converting the brightness (Y)/chrominance (C) signal into the RGB signals, a color space conversion processing circuit 71 for carrying out matrix operation for the spectral image with regard to the RGB signals, and the color space conversion processing circuit 71 outputs spectral image signals of selected wavelength regions $\lambda_1, \lambda_2, \lambda_3$.

The matrix data (one table) used in the matrix operation of the color space conversion processing circuit 71 and stored to the memory 44, the ROM 64 is as shown by Table 1, shown below.

TABLE 1

| Parameter | $k_{pr}$ | $k_{pg}$ | $k_{pb}$ |
|---|---|---|---|
| p1 | 0.000083 | −0.00188 | 0.003592 |
| . | . | . | . |
| . | . | . | . |
| . | . | . | . |
| p18 | −0.00115 | 0.000569 | 0.003325 |
| p19 | −0.00118 | 0.001149 | 0.002771 |
| p20 | −0.00118 | 0.001731 | 0.0022 |
| p21 | −0.00119 | 0.002346 | 0.0016 |
| p22 | −0.00119 | 0.00298 | 0.000983 |
| p23 | −0.00119 | 0.003633 | 0.000352 |
| . | . | . | . |
| . | . | . | . |
| . | . | . | . |
| p43 | 0.003236 | 0.001377 | −0.00159 |
| p44 | 0.003656 | 0.000671 | −0.00126 |
| p45 | 0.004022 | 0.000068 | −0.00097 |
| p46 | 0.004342 | −0.00046 | −0.00073 |
| p47 | 0.00459 | −0.00088 | −0.00051 |
| p48 | 0.004779 | −0.00121 | −0.00034 |
| p49 | 0.004922 | −0.00148 | −0.00018 |
| p50 | 0.005048 | −0.00172 | −3.6E−05 |
| p51 | 0.005152 | −0.00192 | 0.000088 |
| p52 | 0.005215 | −0.00207 | 0.000217 |
| . | . | . | . |
| . | . | . | . |
| . | . | . | . |
| p61 | 0.00548 | −0.00229 | 0.00453 |

The matrix data of Table 1 comprises 61 of wavelength region parameters (coefficient sets) p1 through p61 constituted by dividing, for example, a wavelength region from 400 nm through 700 nm by an interval of 5 nm, and the parameters p1 through p61 are constituted by coefficients $k_{pr}$, $k_{pg}$, $k_{pb}$ (p corresponds to p1 through p61) for matrix operation.

Further, at the color space conversion processing circuit 71, matrix operation of Equation 1, shown below, is carried out by the coefficient $k_{pr}$, $k_{pg}$, $k_{pb}$, and the RGB signal output from the first color converting circuit 70.

Equation 1:

$$\begin{bmatrix} \lambda 1 \\ \lambda 2 \\ \lambda 3 \end{bmatrix} = \begin{bmatrix} k_{1r} & k_{1g} & k_{1b} \\ k_{2r} & k_{2g} & k_{2b} \\ k_{3r} & k_{3g} & k_{3b} \end{bmatrix} \times \begin{bmatrix} R \\ G \\ B \end{bmatrix}$$

That is, when, as λ1, λ2, λ3, for example, parameters p21 (center wavelength 50 nm), p45 (center wavelength 620 nm), p51 (center wavelength 650 nm) of Table 1 are selected, as coefficients ($k_{pr}$, $k_{pg}$, $k_{pb}$), (−0.00119, 0.002346, 0.0016) of p21, (0.004022, 0.000068, −0.00097) of p45, (0.005152, −0.00192, 0.000088) of p51 may be substituted therefor.

Further, the color space conversion processing circuit 71 is provided with a mode selector 72 for selecting either of a spectral image (single color mode) of one wavelength region (narrow band region) and a spectral image (3 colors mode) comprising three wavelength regions, and an amplifying circuit 73 is connected to a post stage of the mode selector 72. The amplifying circuit 73 amplifies λ1, λ2, λ3 signals for forming the spectral image by respective gain values $e_1$, $e_2$, $e_3$, and outputs amplified signals of $e_1 \times \lambda 1$, $e_2 \times \lambda 2$, $e_3 \times \lambda 3$. The amplifying circuit 73 is provided with a second color converting circuit 74 for inputting the signals of λ1, λ2, λ3 as amplified as Rs, Gs, Bs signals for carrying out a processing in correspondence with the RGB signals of the background art and converting the Rs, Gs, Bs signals into the Y/C signal.

The embodiment is constructed by the above-described constitution, first, according to the light source apparatus 14 of FIG. 1, illuminating light is output by driving the lamp driving circuit 51 from the light source lamp 50 by way of the light guide 27, the illuminating window 26, the illuminating light is controlled by the diaphragm 49 in a light amount thereof, at this occasion, the diaphragm position detected by the diaphragm position sensor 52 is supplied to the fourth microcomputer 54. An image of an object illuminated by the illuminating light is taken by CCD 18 of the scope 10, at the scope 10, by driving the CCD driving circuit 19, an image taking signal of the object is output from CCD 18, the signal is amplified by generated double sampling and automatic gain control by the CDS/AGC circuit, thereafter, supplied to the DVP 30 of the processor apparatus 12 as a digital signal by way of the A/D converter 22.

At the DVP 30, various processing are carried out, and the Y/C signal comprising the brightness (Y) signal and the chrominance (R-Y, B-Y) signal is formed. An output of the DVP 30 is normally supplied to the signal processing circuit 32 by way of the switch 31, here, subjected to a predetermined processing, thereafter, supplied to the monitor 15 by way of the D/A converter 35 and the monitor is displayed with a color image of the normal object. Further, according to the embodiment, a spectral image signal can be formed by operating the spectral image-forming circuit 34A by the switch 31 and also the spectral image signal in this case is displayed on the monitor 15 by way of the D/A converter 35.

Figure 5:
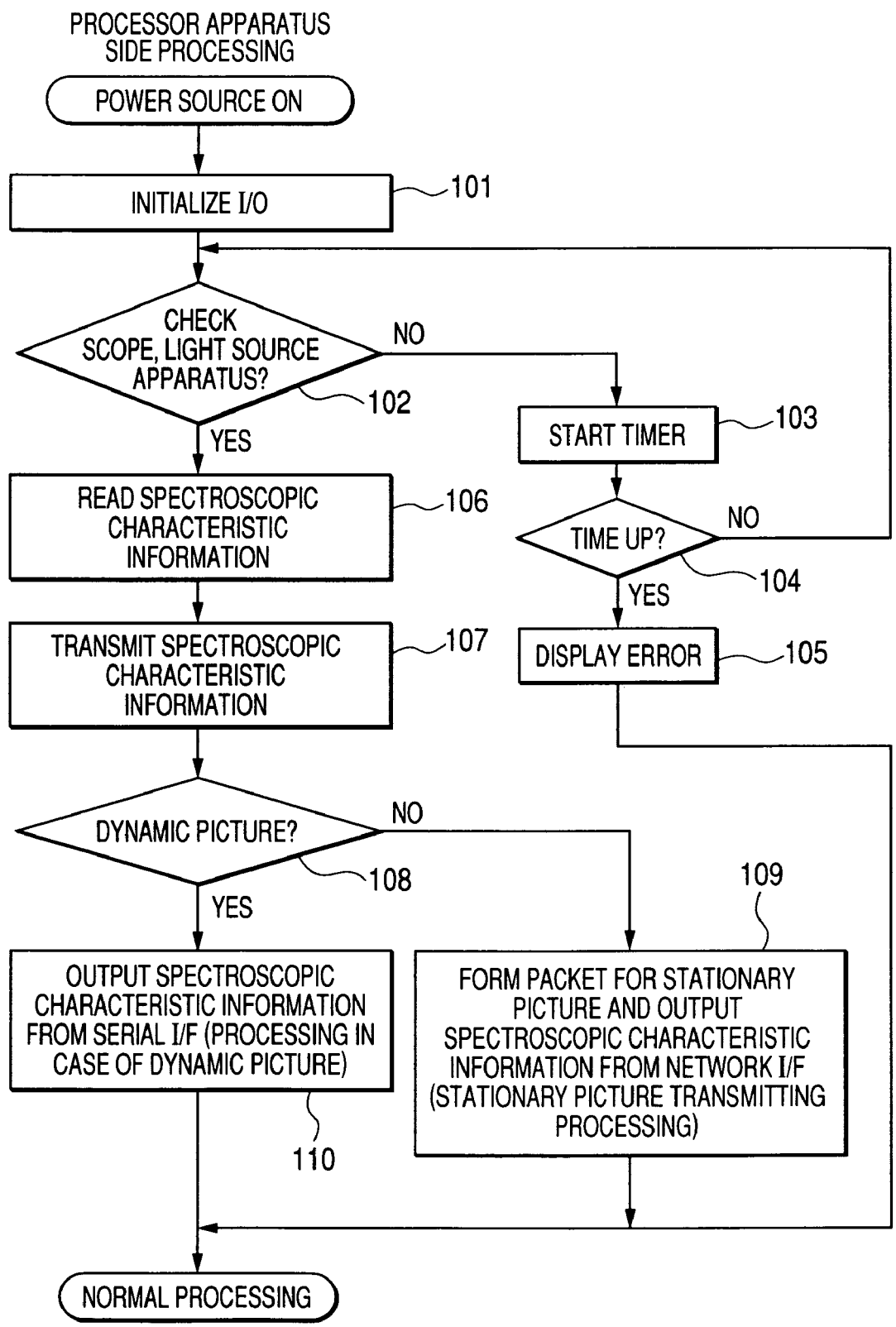
FIG. 5 is a flowchart showing a processing of spectroscopic characteristic information on a side of a processor apparatus of an exemplary embodiment of the invention.

Next, operation in a case in which the stationary picture and the dynamic picture are recorded to the image recording apparatus 16 by recording operation of the scope 10 in reference to FIG. 5 through FIGS. 7A and 7B. FIG. 5 shows a processing on a side of the processor apparatus 12 (microcomputer), when a power source is made ON, after initializing input/output (I/O) (step 101), it is determined whether spectroscopic characteristic information is checked by communication between the microcomputers of the scope 10 and the light source apparatus 14 and the processor apparatus 12 (step 102), when N (No), a timer of a predetermined time period is started (103), when the predetermined time period has elapsed (time up), error is displayed (steps 104, 105). At the step 102, when Y (Yes), after reading the spectroscopic characteristic information (data) (step 106), the spectroscopic characteristic information is transmitted (step 107). At next step 108, it is determined whether the recorded image is the dynamic picture, when N (stationary picture), a packet for the stationary picture adding the spectroscopic characteristic information to the stationary picture data is generated and the packet is output through the network I/F 40, (step 109—stationary picture transmitting processing), when Y (dynamic picture), the spectroscopic characteristic information is output through the serial I/F 45 (step 110—a processing in a case of the dynamic picture).

FIG. 6A shows a stationary picture transmitting processing which is carried out at the step 109, at the packet generating circuit 39, the spectroscopic characteristic information is converted by TAG conversion (converted to a predetermined code) (step 131), the spectroscopic characteristic information converted by TAG conversion is coupled with the stationary picture data (step 132). Next, a file structure is generated (step 133), the packet for the stationary picture is generated (step 134), the packet for the stationary picture is communicated to supply to the image recording apparatus 16 by way of the network I/F 40 (step 135). That is, the spectroscopic characteristic information on the side of the scope with regard to CCD 18 or the like stored to the memory 25 of the scope 10 is supplied from the first microcomputer 24 to the third microcomputer 43 by way of the second microcomputer 42, further, information of the kind of the light source lamp 50 stored to the memory 55 of the light source apparatus 14 (spectroscopic characteristic information) and information of the diaphragm position output from the diaphragm position sensor 52 (spectroscopic characteristic information) is supplied from the fourth microcomputer 54 to the third microcomputer 43 by way of the second microcomputer 42, and the spectroscopic characteristic information is added to the stationary picture data to be communicated.

FIG. 6B shows a processing in case of the dynamic picture carried out at the step 110, the third microcomputer 43 transmits the received spectroscopic characteristic information by way of the serial I/F 45 (step 140).

FIG. 7A shows a stationary picture processing on the side of the image recording apparatus 16, the packet for the stationary picture transmitted from the processor apparatus 12 is input by way of the network I/F 57, when the packet transmission is finished, the image data coupled with the spectroscopic characteristic information is written to be held by the hard disk 61 by way of RAM 65 (step 201). Further, when at a keyboard or the like of the image recording apparatus 16, the wavelength is selected and the spectral image is operated to be displayed (step 202), the spectroscopic characteristic information held in the hard disk 61 is referred, the matrix data (coefficient set) in correspondence of the spectroscopic characteristic information of the scope 10, the light source 14 and the like is selected to be read from the plurality of matrix data of ROM 64 (step 203). Thereafter, at the spectral image-forming circuit 34B, the spectral image based on the matrix data is formed and the spectral image (stationary picture) is output to be displayed on the monitor 15 by way of the D/A converter 68 (step 204).

FIG. 7B shows a dynamic picture processing on the side of the image recording apparatus 16, when the spectroscopic characteristic information is received by way of the serial I/F 58, the spectroscopic characteristic information is transferred to RAM 65 and is primarily stored to be held thereby (step 211). Further, when at the image recording apparatus 16, the wavelength is selected and the spectral image is operated to display (step 212), based on the spectroscopic characteristic information, the corresponding matrix data (coefficient set) is selected to be read from the plurality of matrix data of the ROM 64 (step 213), similar to the case of the static picture, at the spectral image-forming circuit 34B, the spectral image based on the matrix data is formed (step 214), and the spectral image (dynamic picture) is output to be displayed on the monitor 15 by way of the D/A converter 68 (step 215).

Next, an explanation will be given of forming the spectral image at the spectral image-forming circuit 34B shown in FIG. 3 (the same goes also at 34A in the processor apparatus 12). The spectral image is formed (generated) by selecting the wavelength regions of λ1, λ2, λ3 signals by operating the keyboard or the like of the image recording apparatus 16, first, the Y/C (chrominance) signal constituting the image signal stored to the hard disk 61 (in the case of the dynamic picture, output from the video grabber 59) is converted into the RGB signals by the first color converting circuit 70, thereafter, supplied to the color space conversion processing circuit 71 and at the color space conversion processing circuit 71, by the RGB signal data and the matrix data, the matrix operation of Equation 1 is carried out for forming the spectral image. For example, when p21 (center wavelength 500 nm), p45 (center wavelength 620 nm), p51 (center wavelength 650 nm) are selected as the three wavelength regions (λ1, λ2, λ3), the signals of λ1, λ2, λ3 are calculated from the RGB signal data by matrix operation by Equation 2, shown below.

Equation 2:

$$\begin{bmatrix} \lambda 1 \\ \lambda 2 \\ \lambda 3 \end{bmatrix} = \begin{bmatrix} -0.00119 & 0.002346 & 0.0016 \\ 0.004022 & 0.000068 & -0.00097 \\ 0.005152 & -0.00192 & 0.000088 \end{bmatrix} \times \begin{bmatrix} R \\ G \\ B \end{bmatrix}$$

Further, when 3 colors mode is selected by the mode selector 72, the signals of λ1, λ2, λ3 are supplied to the amplifying circuit 73, further, when the single color mode is selected, any signal of λ1, λ2, λ3 is supplied thereto, amplified by the respective gains $e_1, e_2, e_3$ to provide $e_1 \times \lambda 1, e_2 \times \lambda 2, e_3 \times \lambda 3$. The amplified signals output from the amplifying circuit 73 are supplied to the second color converting circuit 74 as the signals of Rs ($=e_1 \cdot \lambda 1$), Gs ($=e_2 \cdot \lambda 2$), Bs ($=e_3 \cdot \lambda 3$), further, when the single color mode is selected, any signal of λ1, λ2, λ3 (for example, when λ2 is selected, $e_2 \cdot \lambda 2$) is supplied to the second color converting circuit 74 as signals of Rs, Gs, Bs. At the second color converting circuit 74, the signals of λ1, λ2, λ3 as the Rs, Gs, Bs signals are converted into the Y/C signal (Y, Rs-Y, Bs-Y), and by supplying the Y/C signal to the monitor 15 by way of the D/A converter 68 (35), the spectral image is displayed on the monitor 15.

Figure 8:
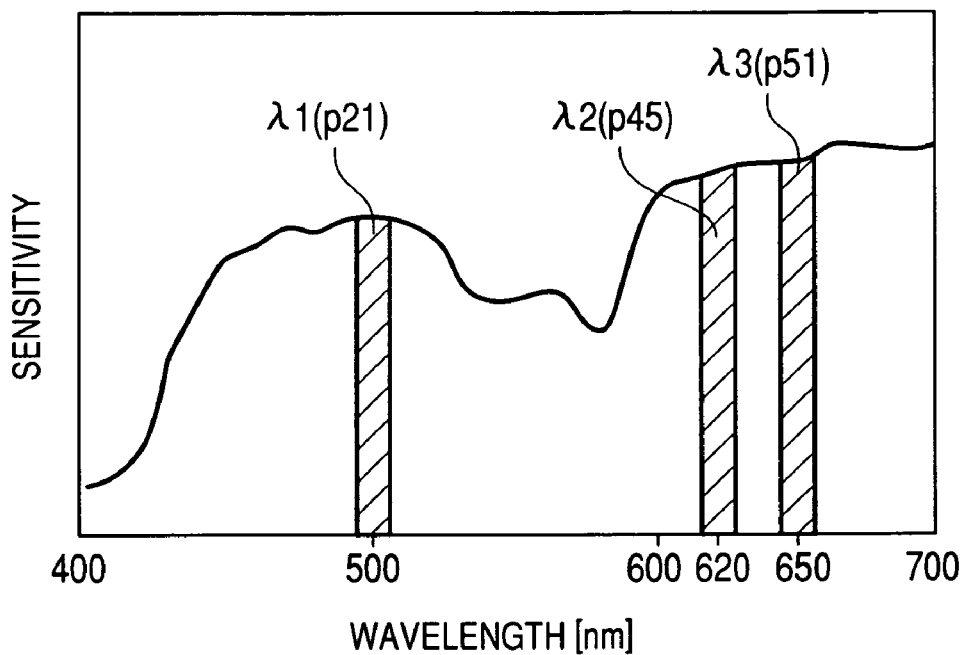
FIG. 8 is a graph diagram showing an example of wavelength regions of a spectral image formed in an exemplary embodiment of the invention along with a reflection spectrum of an organism.
Figure 9:
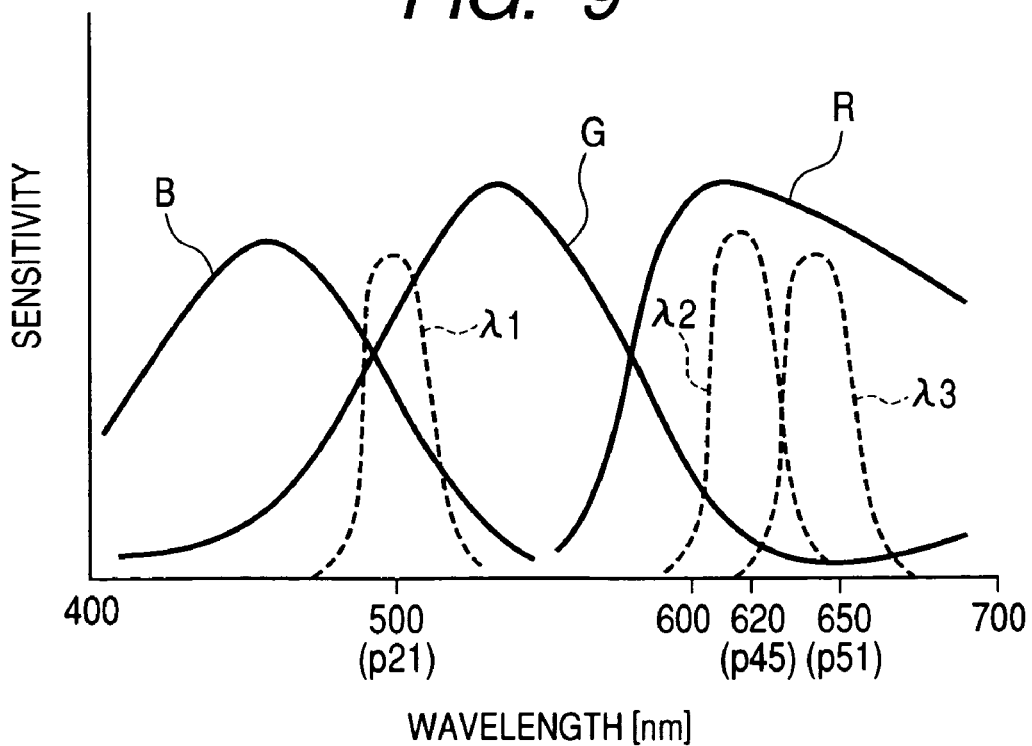
FIG. 9 is a graph diagram showing an example of the wavelength regions of the spectral image formed in an exemplary embodiment of the invention along with a spectroscopic sensitivity characteristic of primary color type CCD.

In this way, the spectral image displayed on the monitor 15 is constituted by color components of the wavelength regions shown in FIG. 8 and FIG. 9. That is, FIG. 8 is a conceptual diagram overlapping the three wavelength regions forming the spectral image on the reflection spector of the organism, further, FIG. 9 is a conceptual diagram overlapping the three wavelength regions on the spectroscopic sensitivity characteristic of CCD 18 of the primary color type (graduations of the color filters and the wavelength regions of the λ1, λ2, λ3 signals do not coincide with each other), according to the embodiment, as illustrated, the wavelengths p21, p45, p51 selected as λ1, λ2, λ3 signals are the color signals of the wavelength regions successively constituting the center wavelengths by 500 nm, 620 nm, 650 nm in a range of about ±10 nm, and the spectral image (dynamic picture and stationary picture) constituted by combining colors of the three wavelength regions is displayed.

Further, the spectral image provided by the image recording apparatus 16 can maintain the reproducibility in the same wavelength regions even when the color image provided by the scope 10 and the light source 14 kinds of which differ is held. That is, the excellent spectral image in which the reproducibility is not dispersed is provided when in the scope 10, the spectroscopic characteristic of CCD 18, the spectroscopic characteristic in consideration of the object optical system, the light guide or the like differ and even when at the light source apparatus 14, the spectroscopic characteristic differs by the difference of whether the light source lamp 50 is the Xenon lamp or the halogen lamp, or by the difference of the diaphragm position of the diaphragm 49, as mentioned later.

Figure 4A:
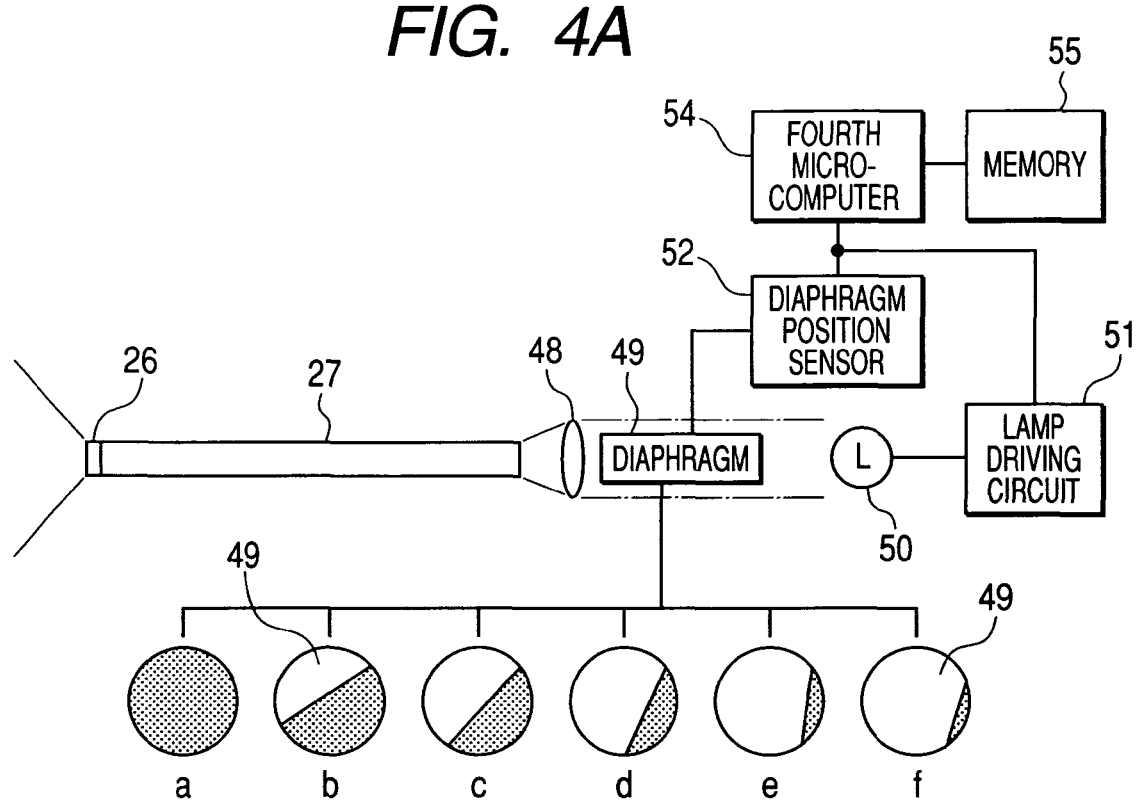
FIGS. 4A and 4B illustrate diagrams showing a constitution and a diaphragm position in a light source apparatus of an exemplary embodiment of the invention (FIG. 4A) and a spectroscopic characteristic at the diaphragm position (FIG. 4B).
Figure 4B:
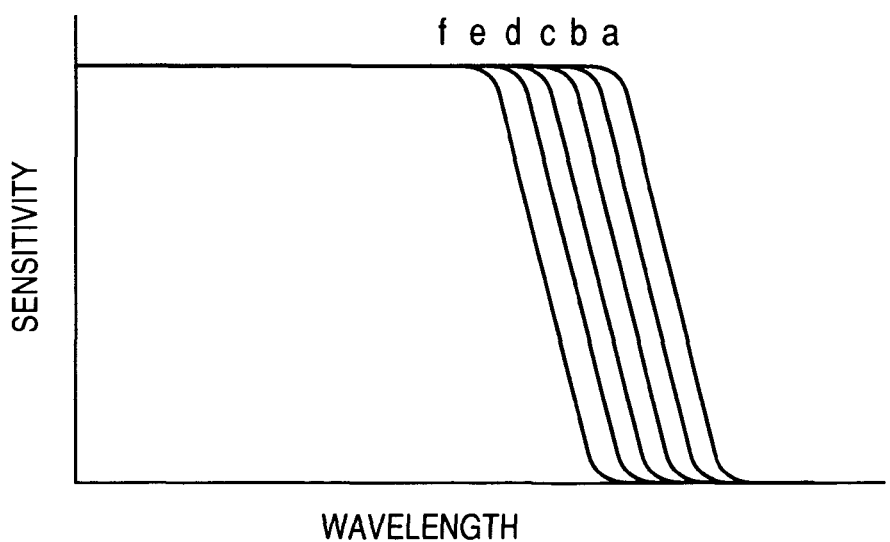

FIGS. 4A and 4B shows the spectroscopic characteristic which is changed by the constitution of the light source 14 and the diaphragm position of an illuminating light (illuminating light amount), according to the embodiment, as shown by FIG. 4A, 6 stages of positions from, for example, a diaphragm position a of full open to diaphragm position f near to full close are detected by the diaphragm position detecting sensor 52, and data of the diaphragm positions a through f is supplied to the image recording apparatus 16 by the fourth microcomputer 54 by way of the third microcomputer 43. Further, at the image recording apparatus 16, the matrix data in correspondence with the diaphragm positions a through f is selected, thereby, the matrix operation is carried out for forming the spectral image.

FIG. 4B shows the spectroscopic characteristic at the position of the diaphragm (blade) 49, according to the diaphragm 49 of the embodiment, the more narrowed from the full open diaphragm position f to the diaphragm position f, the more the spectroscopic characteristic in which the red region component is gradually cut from the side of the long wavelength (a→f) is constituted. Hence, according to the embodiment, the matrix data in correspondence with the diaphragm positions a through f is stored to ROM 64 of the image recording apparatus 16, for example, when the current diaphragm position is c, the matrix data (coefficient set) in correspondence with the diaphragm position c is read from ROM 64 and the operation by the matrix data is carried out. As a result, even when the spectroscopic characteristic of the illuminating light is changed by the diaphragm position, the excellent spectral image having the excellent reproducibility is provided.

According to the example, the spectral image-forming circuit 34A is provided even at the processor apparatus 12, by selecting the wavelength regions of $\lambda 1$, $\lambda 2$, $\lambda 3$ signals by operating the operation panel or the like from the processor apparatus 12, in carrying out observation, treatment by the scope 10, the spectral image can also be formed to be displayed on the monitor 15.

It will be apparent to those skilled in the art that various modifications and variations can be made to the described embodiments of the invention without departing from the spirit or scope of the invention. Thus, it is intended that the invention cover all modifications and variations of this invention consistent with the scope of the appended claims and their equivalents.

The present application claims foreign priority based on Japanese Patent Application No. JP2005-80426 filed Mar. 18 of 2005, the contents of which is incorporated herein by reference.

What is claimed is:

1. An endoscope system apparatus comprising:
   an endoscope comprising an imaging element;
   a signal processor that forms a color image of an object based on an output from the imaging element, the signal processor comprising an information-outputting circuit that outputs each of spectroscopic characteristic information along with a data of the color image, a first storing portion that stores matrix data of a plurality of wavelength regions for forming the spectral image based on the data of the color image, and a first spectral image-forming circuit that performs a matrix operation based on the data of the color image and the matrix data of the plurality of wavelength regions stored in the first storing portion so as to form the spectral image with respect to a selected wavelength region, wherein the spectroscopic characteristic information is for forming a spectral image of the object and includes a spectroscopic characteristic of the imaging element; and
   an image recording apparatus that records the color image output from the signal processor, wherein the image recording apparatus is constituted separately from the signal processor and comprises: a second storing portion that stores matrix data of a plurality of wavelength regions for forming the spectral image based on the data of the color image, the matrix data of the plurality of wavelength regions corresponding to each of the spectroscopic characteristic information output from the information-outputting circuit; and a second spectral image-forming circuit that performs a matrix operation based on the data of the color image and the matrix data of the plurality of wavelength regions stored in the second storing portion so as to form the spectral image with respect to a wavelength region.

2. The endoscope system apparatus according to claim 1, which comprises a light source apparatus that irradiates the object with illuminating light through the endoscope, wherein the light source apparatus provides a spectroscopic characteristic of a light source thereof to the image recording apparatus as the spectroscopic characteristic information, and the spectral image is formed by selecting a matrix data corresponding to the light source.

3. The endoscope system apparatus according to claim 2, wherein
   the light source apparatus comprises a sensor for detecting a diaphragm position of an illuminating light when the color image is formed; and
   the sensor outputs the diaphragm position to the image recording apparatus as the spectroscopic characteristic information, and the spectral image is formed by selecting a matrix data corresponding to the diaphragm position.

4. The endoscope system apparatus according to claim 1, which comprises a display detachably connected with the image recording apparatus, the display displaying the color image and the spectral image.

* * * * *